(12) United States Patent
Severinghaus et al.

(10) Patent No.: US 8,232,382 B2
(45) Date of Patent: Jul. 31, 2012

(54) AVIAN SEX IDENTIFICATION OLIGONUCLEOTIDES

(75) Inventors: Lucia Liu Severinghaus, Taipei (TW);
Lih-Chiann Wang, Yonghe (TW);
Chi-Tsong Chen, Taipei (TW)

(73) Assignee: Academia Sinica, Taipei (TW)

( * ) Notice: Subject to any disclaimer, the term of this patent is extended or adjusted under 35 U.S.C. 154(b) by 409 days.

(21) Appl. No.: 12/339,178

(22) Filed: Dec. 19, 2008

(65) Prior Publication Data

US 2009/0203539 A1 Aug. 13, 2009

Related U.S. Application Data

(60) Provisional application No. 61/018,103, filed on Dec. 31, 2007.

(51) Int. Cl.
| | |
|---|---|
| C07H 21/02 | (2006.01) |
| C40B 20/00 | (2006.01) |
| C40B 20/02 | (2006.01) |
| C40B 30/04 | (2006.01) |
| C40B 40/06 | (2006.01) |

(52) U.S. Cl. ............... 536/24.31; 536/23.1; 536/23.5; 536/24.3; 506/2; 506/3; 506/9; 506/16

(58) Field of Classification Search .............. None
See application file for complete search history.

(56) References Cited

U.S. PATENT DOCUMENTS

| 5,508,165 A | 4/1996 | Halverson et al. |
| 5,707,809 A | 1/1998 | Halverson et al. |
| 2003/0191297 A1 | 10/2003 | Griffiths et al. |
| 2004/0241658 A1* | 12/2004 | Barrett et al. ............ 435/6 |

OTHER PUBLICATIONS

Sundstrom et al. (Is the Rate of Insertion and Deletion Mutation Male Biased?: Molecular Evolutionary Analysis of Avian and Primate Sex Chromosome Sequences, 2003, Genetics, vol. 164, pp. 259-268.*
Arima et al. (GenEmbl accession No. AB279887, submitted Oct. 25, 2006, accessed Apr. 1, 2011, 2 pages, attached).*
Ito et al. (GenEmbl accession No. AB112944, submitted Jun. 22, 2003, accessed Apr. 1, 2011, 2 pages, attached.*
Garcia-Moreno et al. (Rooting a Phylogeny with Homologous Genes on Opposite Sex Chromosomes (Gametologs): A Case Study Using Avian CHD, 2000, Molecular Biology and Evolution, vol. 17, pp. 1826-1832).*
Bartosch-Harlid et al. (Life history and the male mutation bias, 2003, Evolution, vol. 57, pp. 2398-2406, and attached SCORE report, 11 total pages).*

* cited by examiner

*Primary Examiner* — Amber D Steele
*Assistant Examiner* — Shannon Janssen
(74) *Attorney, Agent, or Firm* — Occhiuti Rohlicek & Tsao LLP (57) ABSTRACT

This invention relates to a number of bird sex-identification oligonucleotides and their use in determining the sex of birds in various families.

10 Claims, 6 Drawing Sheets

```
       |------ 1237L                                              Probe W1 GGTTGGGTGGTTTTTCGTTG
Con  GAGAAACTGTGCAAAACAGGTGTGTTTTGGTTTTGATTAACTAACTTTTATTTTTTGTTGTTGTTGGTTTGTTTGTTTTGGTTGTTGTTGTGTTTTGGTTGGTGTGT EuW  .............. .....A...C.G.........CC..........G...A................G.G.........C....C........-....G.....G....... 109
EuZ  ............................C........C.......--.G.....C..CA..GC......A.-..A............GGG.A...C......G............G..-. 108
                                                                                      Probe ZW1 CTGAAATTCCAGATCAGCT
Con  TTTTTGCTTGGCATTCTGACTGCCCTATTTTTGACAGGCTAGGTAACACTTTACTTACATTTTTTGGTCACGTAGCTTTGAACTACTTACTCTGAAATTCCAGATCAGCT EuW  ..CA...A.....CC.CC..CA................A....A......A...ACA.A.......A...................A.... ................ 219
EuZ  .....C.........----.....A...A-..............A...........G..A...A.................................................. 211
     TTAATGGAAGTGAAGG
Con  TTAATGGAAGTGAAGGGAGGCGCAGTAGGAGCAGAAGATATTCTGGA
                       1272H ------|

EuW  ................AA.............................  266
EuZ  ................................................  258
```

Fig. 1

```
                                                                    Probe W1  GGTTGGGTGGTTTTTCGTTG
Con  GAGAAACTGTGCAAAACAGGTGTGTTTTGGTTTTGATTAACTAACTTTTATTTTTTTGTTGTTGTTGGTTTGTTTGTTTTTGGTTGTTGTTGTGTTTTTGGTTGGTGTGT EuW  .................A...C..G........CC..........G...A...............G..G..G.....C....C......-..G....G.......  109
EuZ  .................C.....C......--..G.....C..CA..GC.....A.-..A...........GGG..A...C.......G..............G..-.  106
                                                                             Probe ZW1  CTGAAATTCCAGATCAGCT
Con  TTTTTGCTTGGCATTCTGACTGCCCTATTTTTGACAGGCTAGGTAACACTTTACTTACATTTTTTGGTCACGTAGCTTTGAACTACTTACTCTGAAATTCCAGATCAGCT EuW  ..CA...A.....CC..CC...CA..............A....A......A...ACA..A......A...........A.... ................  219
EuZ  .....C..-----....A...A-..............A.............G..A...A.............................................  211

TTAATGGAAGTGAAGG
Con  TTAATGGAAGTGAAGGGAGGCGCAGTAGGAGCAGAAGATATTCTGGA
                                         1272H ---|

EuW  ...........AA..............................  266
EuZ  ...........................................  258
```

| | | | |
|---|---|---|---|
| King Penguin♂<br>*Aptenodytes patagonicus*<br>(Spheniscidae) | King Penguin♀<br>*Aptenodytes patagonicus*<br>(Spheniscidae) | Caribbean Flamingo♂<br>*Phoenicopterus rubber*<br>(Phoenicopteridae) | Caribbean Flamingo♀<br>*Phoenicopterus rubber*<br>(Phoenicopteridae) |
| Crested Goshawk♂<br>*Accipiter trivirgatus*<br>(Accipitridae) | Crested Goshawk♀<br>*Accipiter trivirgatus*<br>(Accipitridae) | Swinhoe's Pheasant♂<br>*Lophura swinhoii*<br>(Phasianidae) | Swinhoe's Pheasant♀<br>*Lophura swinhoii*<br>(Phasianidae) |
| Helmeted guineafowl♂<br>*Numida meleagris*<br>(Numididae) | Helmeted guineafowl♀<br>*Numida meleagris*<br>(Numididae) | Sarus Crane♂<br>*Grus antigone*<br>(Gruidae) | Sarus Crane♀<br>*Grus antigone*<br>(Gruidae) |
| Nicobar Pigeon♂<br>*Caloenas nicobarica*<br>(Columbidae) | Nicobar Pigeon♀<br>*Caloenas nicobarica*<br>(Columbidae) | Light-vented Bulbul♂<br>*Pycnonotus sinensis*<br>(Pycnonotidae) | Light-vented Bulbul♀<br>*Pycnonotus sinensis*<br>(Pycnonotidae) |

| | | | |
|---|---|---|---|
|  |  |  |  |
| Formosan Magpie♂ *Urocissa caerulea* (Corvidae) | Formosan Magpie♀ *Urocissa caerulea* (Corvidae) | Island Canary♂ *Serinus canaria* (Fringillidae) | Island Canary♀ *Serinus canaria* (Fringillidae) |
|  |  |  |  |
| Mountain Scops-owl♂ *Otus spilocephalus* (Strigidae) | Mountain Scops-owl♀ *Otus spilocephalus* (Strigidae) | Tawny Fish-owl♂ *Ketupa flavipes* (Strigidae) | Tawny Fish-owl♀ *Ketupa flavipes* (Strigidae) |
|  |  |  |  |
| Common Flameback♂ *Dinopium javanense* (Picidae) | Common Flameback♀ *Dinopium javanense* (Picidae) | Blue-and-Yellow Macaw♂ *Ara ararauna* (Psittacidae) | Blue-and-Yellow Macaw♀ *Ara ararauna* (Psittacidae) |

SEQUENCE LISTING

```
<160> NUMBER OF SEQ ID NOS: 22

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ctgraattcc agatcagctt yaatggaary gaagg                              35

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atmtcttyag agrcttgayg gatcaataaa agg                                33

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
```

-continued

<400> SEQUENCE: 3
ggttgggtgg tttttcgttg                                          20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
agagytggac acagcactgm ag                                       22

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
ggtctcatga gagtggagta cag                                      23

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cttttgkgtt gkgtgrtttt                                          20

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
atttwtraaa gtttmatttt atgtayagra a                             31

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggttgggtgg tttttcgttg                                          20

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

-continued

```
gttgttttgg tctttatttt tgg                                            23

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctgatgaatt agaaagatga artg                                           24

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
attttatttt atgtacagga aaagactg                                       28

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
atgaagcatg tcagggcttg gatacctcg                                      29

<210> SEQ ID NO 13
<211> LENGTH: 267
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 13
gagaaactgt gcaaaacagg tgtgttttgg ttttgattaa ctaacttta ttttttgtt     60 gttgttggtt tgtttgtttt tggttgttgt tgtgttttgg tttggtgtgt tttttgcttg  120
gcattctgac tgccctattt tgacaggct aggtaacact ttacttacat tttttggtca  180
cgtagctttg aactacttac tctgaaattc cagatcagct ttaatggaag tgaagggagg  240
cgcagtagga gcagaagata ttctgga                                      267

<210> SEQ ID NO 14
<211> LENGTH: 266
<212> TYPE: DNA
<213> ORGANISM: Bubo bubo

<400> SEQUENCE: 14
gagaaactgt gcaaaacagg tatgtctggg ttttgaccaa ctaactttga ttattttgtt   60
gttgttggtt gggtggtttt tcgttgctgt tgttttgggt tgggtgtgtt tcatgcatgg  120
cacccccacc accctatttt tgacagacta gataacacat taacaaaatt ttttagtcac  180
gtagctttga actacttaat ctgaaattcc agatcagctt taatggaagt gaagggaaac  240
gcagtaggag cagaagatat tctgga                                       266
```

<210> SEQ ID NO 15
<211> LENGTH: 258
<212> TYPE: DNA
<213> ORGANISM: Bubo bubo

<400> SEQUENCE: 15

```
gagaaactgt gcaaaacagg tgtcttttgg ttctgattcg aacttctaca ttgctgttga    60
tttagtttgt tgttggggga ttcttgttgg gttttggttt ggggtttttt tccttttctg   120
aatgcatatt tttgacaggc taggtaaaac tttacttaca tttgttgatc acatagcttt   180
gaactactta ctctgaaatt ccagatcagc tttaatggaa gtgaagggag gcgcagtagg   240
agcagaagat attctgga                                                 258
```

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16

```
ctgaaattcc agatcagctt taatggaagt gaagg                               35
```

<210> SEQ ID NO 17
<211> LENGTH: 1023
<212> TYPE: DNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (1000)..(1001)
<223> OTHER INFORMATION: a or not present
<220> FEATURE:
<221> NAME/KEY: modified_base
<222> LOCATION: (1002)..(1002)
<223> OTHER INFORMATION: a, g or not present
<220> FEATURE:
<221> NAME/KEY: modified_base
<222> LOCATION: (1003)..(1003)
<223> OTHER INFORMATION: c or not present
<220> FEATURE:
<221> NAME/KEY: modified_base
<222> LOCATION: (1004)..(1005)
<223> OTHER INFORMATION: a or not present
<220> FEATURE:
<221> NAME/KEY: modified_base
<222> LOCATION: (1006)..(1006)
<223> OTHER INFORMATION: g or not present
<220> FEATURE:
<221> NAME/KEY: modified_base
<222> LOCATION: (1007)..(1007)
<223> OTHER INFORMATION: c or not present
<220> FEATURE:
<221> NAME/KEY: modified_base
<222> LOCATION: (1008)..(1008)
<223> OTHER INFORMATION: a or not present
<220> FEATURE:
<221> NAME/KEY: modified_base
<222> LOCATION: (1009)..(1009)
<223> OTHER INFORMATION: c or not present
<220> FEATURE:
<221> NAME/KEY: modified_base
<222> LOCATION: (1010)..(1010)
<223> OTHER INFORMATION: t or not present
<220> FEATURE:
<221> NAME/KEY: modified_base
<222> LOCATION: (1011)..(1012)
<223> OTHER INFORMATION: g or not present

```
<220> FEATURE:
<221> NAME/KEY: modified_base
<222> LOCATION: (1013)..(1013)
<223> OTHER INFORMATION: a or not present
<220> FEATURE:
<221> NAME/KEY: modified_base
<222> LOCATION: (1014)..(1014)
<223> OTHER INFORMATION: t or not present
<220> FEATURE:
<221> NAME/KEY: modified_base
<222> LOCATION: (1015)..(1015)
<223> OTHER INFORMATION: c or not present
<220> FEATURE:
<221> NAME/KEY: modified_base
<222> LOCATION: (1016)..(1016)
<223> OTHER INFORMATION: a or not present
<220> FEATURE:
<221> NAME/KEY: modified_base
<222> LOCATION: (1017)..(1018)
<223> OTHER INFORMATION: t or not present
<220> FEATURE:
<221> NAME/KEY: modified_base
<222> LOCATION: (1019)..(1019)
<223> OTHER INFORMATION: c, t or not present
<220> FEATURE:
<221> NAME/KEY: modified_base
<222> LOCATION: (1020)..(1020)
<223> OTHER INFORMATION: c or not present
<220> FEATURE:
<221> NAME/KEY: modified_base
<222> LOCATION: (1021)..(1022)
<223> OTHER INFORMATION: a or not present
<220> FEATURE:
<221> NAME/KEY: modified_base
<222> LOCATION: (1023)..(1023)
<223> OTHER INFORMATION: t or not present

<400> SEQUENCE: 17
gttagagtct gattttctct cagatggtga ggatgttagg catcctagca gagtatttga      60
agtatcgtca gttttccttt caggtaagaa ttttgctggt agtacagaat catagaatgg     120
tttggggttga gagggacctt aaagatcatc tagttccaac cctgctatgg gcagggacat    180
cttcactaga caggatgttt gaagtctcgt ccagtttggc cttgaacact ttcaggtagg     240
agcaccacac ttctctgggt gacctgttcc agtgtctacc accctcatag tcaagaattt     300
cttctttgta tctagtctga atctacccct ctttcagttta aaacagttac ctcttgtttt    360
atcgctacac tctctgataa gagggttcct cccccccctt tcctataggc cctttaagta     420
ctggaaggct gctatgagtt gtccccagag tctcctcttc tctaggctgg acattccgaa     480
ctccttcgtc ctctggtcat gttcttgggc tcctctggac ctgttttagc tggtctgtgt     540
ccttcttgtg tgggggtccc agagttggac acagcactga ggggggggga tgatttcatg    600
agagtggagt acagagggag aatcatctttt cttgacctgc tggctacgct tctcttgatg    660
cagccctgga tacagttggt tttctgtagt cgttatgaag ccttgatctt taccactttg     720
tcttaagaaa agtgtccttt ttgtaggaag atttgtcaaa gtttaatttt ctgtacaggg     780
aaagactgtc aattgctata tgctatatag tattttgaaa tgaaactgat gaattagaaa     840
tattatgtga attgtttcat ttcttccccc tcccctaatt gttttggcag ttgggaattc     900
aagttgctcc gattttgaat atagtatagg aattaccttt ttaactgtat tatcaatctc     960
ttgaagagac ttgatggatc aataaaaggg gaattgagan nnnnnnnnn nnnnnnnnnn    1020
nnn                                                                  1023

<210> SEQ ID NO 18
<211> LENGTH: 1001
<212> TYPE: DNA
<213> ORGANISM: Bubo flavipes
```

```
<220> FEATURE:
<221> NAME/KEY: modified_base
<222> LOCATION: (964)..(964)
<223> OTHER INFORMATION: a, c, g, t, unknown or other
<220> FEATURE:
<221> NAME/KEY: modified_base
<222> LOCATION: (966)..(966)
<223> OTHER INFORMATION: a, c, g, t, unknown or other
<220> FEATURE:
<221> NAME/KEY: modified_base
<222> LOCATION: (979)..(979)
<223> OTHER INFORMATION: a, c, g, t, unknown or other

<400> SEQUENCE: 18
ggggtcagag tatgattttc tctcagatgg tgaggatgct agacatccta gcagagtatt      60
tgaagtatcg tcagtttccc tttcaggtaa gaattttgct ggtagtacag aatcatagaa     120
tggtttgggt tgaaagggac cttaaagatc atctagttcc aaccctgcc atgggcaggg      180 acaccttcca ctagatcagg ttgctcaaag ccccgtccaa cctggccttg aacacttcca     240 gggaggggc aaccacagct tctctgggca acctgttcca gtgtctcacc accctcacag      300
taaagaattt cttctttata tctagtctaa atctaccctc tttcagttta aaacagttac     360
cccttgtcct atcgctacac tccctgataa aagagttcct ccccacccct ttcctatagg     420
ccctctttaa gtactggaag gctgctataa ggtgtcccca gagccttctc ttctctaggc     480
tgaacaaccc ctactccttc atcctccgat catctttgtg gcctcctctg acccgctcc      540 agcaggtcca tgtccttctt atgtgggggt cccagagtt ggacacagca ctgcagggg      600 gggtctcatg agagtggagt acagtgggag aatcacctcc ctcgacccgc tggctacgct     660
tctcttgatg cagccctgga tacagttggc tttctgtagt agctaagaag ccttgatctt     720
taccacttta tcttaagaaa agtgtccttt ttgtagaaag atttatcaaa gtttaatttt     780
atgtacagga aaagactctc aattactata tgctaaatag tattttgaaa tgaaactgat     840
gaattagaaa aatgaggtgc atacattact cttatccccc cccccaatt gttttggcaa      900 ttgagaattc aagttgctcc aattagaata tagtaggaat ccttttaac tgtcttattc      960 aatngnggga agagacttna tggagcaaaa aagggaatag a                          1001

<210> SEQ ID NO 19
<211> LENGTH: 998
<212> TYPE: DNA
<213> ORGANISM: Otus elegans
<220> FEATURE:
<221> NAME/KEY: modified_base
<222> LOCATION: (5)..(5)
<223> OTHER INFORMATION: a, c, g, t, unknown or other
<220> FEATURE:
<221> NAME/KEY: modified_base
<222> LOCATION: (963)..(963)
<223> OTHER INFORMATION: a, c, g, t, unknown or other

<400> SEQUENCE: 19
gagtntgatt ttctctcaga tggtgaggat gctagacatc ctagcagagt atttgaagta      60
tcgtcagttt cccttcagg taagaatttt gctggtagta cagaatcata gaatggtttg      120
ggttgaaagg gaccttaaag atcatctagt tccaacctct gccatgggca ggacacctt       180 tcactagacc aggctgctca aagcccatc aacctggcc ttgaacactt ccagggagga       240
gacatccaca acttctctgg gcaacctgtt ccagtgtctg accaccctca aataaagaa      300 tttcttcttt atatctagtc taaatctacc ctctttcagt ttaaaacagt taccccttgt     360
cctatcgcta cactccctga taagagttcc tccccgcccc tttcctatag gtcccctta      420 agtactggaa ggctgctata aggtgtcccc agagcctcct cttctctagg ctgaacaacc     480
```

```
ccaactccctt catcctccga tcatcttcgt ggcctcctct ggacccgctc cagcaggtcc      540
atgtccttct tatgtggggg ttcccagagc tggacacagc actgaagggg ggggggaggt      600
ctcatgagag tggagtacag ggggagaatc acctcccttg acccgctggc tacgcttctc      660
ttgatgcagc cctggataca gttggctttc tgtagtagct aagaagcctt gatctttacc      720
actttatctt aagaaaagtg tccttttttgt agaaagattt atcaaagttt aattttatgt      780
acaggaaaat actctcaatt actatatgct aaatagcatt ttgaaattaa actgatgaat      840
tagaaagatg aggtgttact cttatctccc cccctcccc caattgtttt tgcaattgag       900
aattcaagtt gctccaatta gaatatagta ggagttgcct ttttaactgt attatcaatc      960
tcnggaagag actgatggag caataaaagg gaatgaga                              998
```

```
<210> SEQ ID NO 20
<211> LENGTH: 641
<212> TYPE: DNA
<213> ORGANISM: Bubo flavipes

<400> SEQUENCE: 20
gttactgatt cgtctacgag aacgtggcaa cagagttctg atttctcac agatggtgag        60 aatgctggac atcctagcag aatatctgaa gtatcgtcag tttccttttc aggtaagaat      120
cttggtggta atagccaaga aactttgatc ttgaatatga gaaaaacctc ttctttactc      180
tgagggtgac agagcactgg aacgagttgt ccagaatctc catcctctga gacattcaga      240
agtcacctgg tcatgacctt gggcaacctg ttttagctgt ctgtgcctga gtaggggagt      300
tagacaagat gacttccaga ggtccttccc aacctcaacc attttgtcat tatgtgatct      360
ttaccacttt gcttaagaaa agatataaga aaatgtgttc ttttttctaga aagactggca      420 attgctatat gctatatagt attttgaaat gaaacataaa ttaaatatat atgtgaagtg      480
ttgcattact tcacataaca gttttggcag ttgggaattc aggttgctca gattttgaat      540
atagtataag gattactctt taactgtagt atcaatctct tcagagactt gatggatcaa      600
taaaagggga attgaggaaa caagcactgg atcattccaa t                         641
```

```
<210> SEQ ID NO 21
<211> LENGTH: 644
<212> TYPE: DNA
<213> ORGANISM: Otus elegans

<400> SEQUENCE: 21
gttactgatt cgtctacgag aacgtggcaa cagagttctg atttctcac agatggtgag        60 aatgctggac atcctagcag aatatctgaa gtatcgtcag tttccttttc aggtgagaat      120
ctgggtggta ataaccaaga aactttgatc ttgaatataa gaaaaacctc ttatttactc      180
tgagggtgac agagcactgg aacgagttgt ccagaatctc catcctcttg agacattcag      240
aagtcacctg gtcatgacct tgggcaacct gttttagctg tctgtgcctg agtaggggag      300
ttagacaaga tgacttccag aggtccttcc taacctcaac cattttgtca ttatgtgatc      360
tttaccactt tgcttaagat ataagaaaat gtgttctttt tctagaaaga ctggcaattg      420
ctatatgcta tatagtattt tgaaatgaaa cataagttaa aatattatgt gaaatgttgc      480 attactttt cttcacataa cagttttggc agttgggaat tcaagttgct cagattttga      540
atatagtata agaattagtc tttaactgta gtatcaatct cttcagaggc ttgaccggat      600
caataaaagg ggaattgaga aagcaagcac tggatcattt caat                      644
```

```
<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
atctcttcag agrcttgayg gatcaataaa agg                                    33
```

AVIAN SEX IDENTIFICATION OLIGONUCLEOTIDES

CROSS-REFERENCE TO RELATED APPLICATION

This application claims the benefit of U.S. Provisional Application 61/018,103, filed Dec. 31, 2007, the content of which is incorporated herein by reference in its entirety.

BACKGROUND OF THE INVENTION

Sex identification is important in bird breeding and conservation. However, birds of many families are sexually monomorphic, rendering it difficult to identify their sex via appearance.

Genetic variances have been found between the chromohelicase-DNA-binding protein 1 (CHD1) gene located on W chromosome (the female bird-specific sex chromosome) and its counterpart located on Z chromosome (the mutual sex chromosome of both male and female birds). More specifically, two CHD1 introns exhibit length differences between their W and Z counterparts. See Fridolfsson et al., 1999; Kahn et al., 1998; and Griffiths et al., 1998. These intron length differences were utilized to determine the sex of some non-ratite birds. See Griffiths et al. 1998; and Jensen et al. 2003. This approach, however, is not applicable to birds in many families, e.g., Strigidae, as the length differences are indiscernible in these families. See Kahn et al., 1998; and Fridolfsson and Ellegren 1999.

Thus, there is a need to develop a new sex-determining method that is applicable to a large number of bird families.

SUMMARY OF THE INVENTION

The present invention is based on the discovery of a number of novel bird sex-identification oligonucleotides and their successful application in determining the sex of birds in various families.

Accordingly, one aspect of this invention features the following bird sex-identification oligonucleotides:

ZW1 and ZW1c, including the nucleotide sequence of 5'-CTGRAATTCCAG ATCAGCTTYAATGGAARYGA-AGG-3' (SEQ ID NO:1) and its complementary sequence, respectively;

ZW2 and ZW2c, including the nucleotide sequence of 5'-ATMTCTTYAGAGR CTTGAYGGATCAATAAAAGG-3' (SEQ ID NO:2) and its complementary sequence, respectively;

W1 and W1c, including the nucleotide sequence of 5'-GGTTGGGTGGTTTTT CGTTG-3' (SEQ ID NO:3) and its complementary sequence, respectively;

W2 and W2c, including the nucleotide sequence of 5'-AGAGYTGGACACAGC ACTG MAG-3' (SEQ ID NO:4) and its complementary sequence, respectively;

W3 and W3c, including the nucleotide sequence of 5'-GGTCTCATGAGAG TGGAGT ACAG-3' (SEQ ID NO:5) and its complementary sequence, respectively;

W4 and W4c, including the nucleotide sequence of 5'-CTTTTGKGTTGKGTG RTTTT-3' (SEQ ID NO:6) and its complementary sequence, respectively;

W5 and W5c, including the nucleotide sequence of 5'-ATTTWTRAAAGTTTM ATTTTATGTAYAGRAA-3' (SEQ ID NO:7) and its complementary sequence, respectively;

W6 and W6c, including the nucleotide sequence of 5'-GGTTGGGTGGTTTTTCGTTG-3' (SEQ ID NO:8) and its complementary sequence, respectively;

W7 and W7c, including the nucleotide sequence of 5'-GT-TGTTTTGGTCTTTA TTTTT GG-3' (SEQ ID NO:9) and its complementary sequence, respectively;

W8 and W8c, including the nucleotide sequence of 5'-CT-GATGAATTAGAAA GATG AARTG-3' (SEQ ID NO:10), and its complementary sequence, respectively; and W9 and W9c, including 5'-ATTTTATTTTATGTACAG-GAAAAGACTG-3' (SEQ ID NO:11) and its complementary sequence, respectively. (R: A/G; Y: T/C; K: G/T; M: A/C; S: C/G; and W: A/T)

Any of the above-described oligonucleotides can further include a poly T tail (e.g., containing up to 19 Ts) at its 5' or 3' end. The term "oligonucleotide" used herein refers to a nucleic acid having up to 60 nucleotides.

Another aspect of this invention features a kit for detecting bird sex, including two sets of oligonucleotides: the first set includes one or more of W1, W1c, W2, W2c, W3, W3c, W4, W4c, W5, W5c, W6, W6c, W7, W7c, W8, W8c, W9, and W9c; and the second set includes one or more of ZW1, ZW1c, ZW2, and ZW2c. Optionally, the kit further includes a positive control oligonucleotide, a negative control oligonucleotide, or both. In one example, the kit contains a first oligonucleotide set including W1, W2, W3, W4, W5, W6, W7, W8, and W9; and a second oligonucleotide set including ZW1 and ZW2. When the kit is used for determining the sex of a bird of Strigidae, the first oligonucleotide set preferably includes one or more of W1, W1c, W2, W2c, W3, and W3c. For example, such a kit can contains W1, W2, W3, ZW1, and ZW2. When the kit of this invention is used for determining the sex of a bird of Accipitridae, Columbidae, Corvidae, Fringillidae, Gruidae, Numididae, Phasianidae, Phoenicopteridae, Picidae, Psittacidae, Pycnonotidae, Spheniscidae, or Strigidae, the first oligonucleotide set includes one or more of W3, W3c, W4, W4c, W5, W5c, W6, W6c, W7, W7c, W8, W8c, W9, and W9c. In one example, the kit contains W3, W4, W5, W6, W7, W8, W9, ZW1, and ZW2.

All of the oligonucleotides contained in any of the above-described kits can be attached to a suitable supporting member, e.g., a polymer substrate, to form a DNA chip.

The kit of this invention is used for detecting the sex of a bird by hybridizing the two sets of oligonucleotides contained therein with a DNA sample obtained from the bird. The DNA sample hybridizable to both the first and second sets of oligonucleotides indicates that it is from a female bird; the DNA sample hybridizable to only the second set of oligonucleotides indicates that it is from a male bird.

The details of one or more embodiments of the invention are set forth in the description below. Other features or advantages of the present invention will be apparent from the following detailed description of several examples and also from the appended claims.

DETAILED DESCRIPTION OF THE INVENTION

Described herein are two sets of avian sex-identification oligonucleotides. The first set of oligonucleotides, including W1, W1c, W2, W2c, W3, W3c, W4, W4c, W5, W5c, W6, W6c, W7, W7c, W8, W8c, W9, and W9c, are hybridizable to W chromosome-specific intron sequences of the CHD1 gene, and therefore are female-bird specific. In particular, W1, W1c, W4, W4c, W6, W6c, W7, and W7c are hybridizable to the intron flanked by primers 1237L and 1272H (see Kahn et al. 1998); and W2, W2c, W3, W3c, W5, W5c, W8, W8c, W9, and W9c are hybridizable to the intron flanked by primers 2550F and 2718R (see Fridolfsson and Ellegren 1999). The second set of oligonucleotides, including ZW1, ZW1c, ZW2, and ZW2c, are hybridizable to Z-specific intron sequences of the CHD1 gene. More specifically, ZW1 and ZW1c are hybridizable to the intron flanked by primers 1237L/1272H; and ZW2 and ZW2c are hybridizable to the intron flanked by primers 2550F/2718R. An oligonucleotide hybridizable to a target sequence refers to an oligonucleotide capable of forming base pairs with the target sequence under suitable hybridization conditions, such as hybridization at 50-60° C. and washing with <0.5×SSC (e.g., 0.2×SSC, 0.1×SSC, or any equivalent wash buffer) at 55-60° C.

Both the first and second sets of the oligonucleotides can be made by chemical synthesis. Preferably, they are immobilized on a polymer substrate via a linker (e.g., a poly T tail included in the oligonucleotides) to form a DNA chip. Each DNA chip should contain at least one oligonucleotide from the first oligonucleotide set and at least one from the second oligonucleotide set. Optionally, the DNA chip further contains a positive control oligonucleotide, which can have any nucleotide sequence as long as its complementary sequence does not hybridize with any of the other oligonucleotides immobilized on the same chip. The DNA chip can also contain a negative control oligonucleotide, i.e., an oligonucleotide that does not hybridize to bird DNA.

The first and second sets of sex-identification oligonucleotides described herein can be used for determining the sex of birds in various families, e.g., Accipitridae, Anatidae, Ardeidae, Bucerotidae, Columbidae, Corvidae, Cracidae, Falconidae, Fringillidae, Gruidae, Musophagidae, Numididae, Paradisaeidae, Phalacrocoracidae, Phasianidae, Phoenicopteridae, Picidae, Ploceidae, Procellariidae, Psittacidae, Pycnonotidae, Ramphastidae, Spheniscidae, Strigidae, Threskiornithidae, or Timaliidae. More specifically, a bird's sex is determined by hybridizing its DNA under suitable hybridization conditions with both the first and second sets of the oligonucleotides, which preferably are immobilized on a DNA chip. The bird DNA can be genomic DNA prepared by a conventional method, or PCR products amplified therefrom that contain the CHD1 intron flanked by primers 1237L/1272H and/or the CHD1 intron flanked by primers 2550F/2718R. If the DNA obtained from a bird is hybridizable to oligonucleotides of both the first and second sets, it indicates that the bird is female. On the other hand, if the DNA only hybridizes to oligonucleotides of the second set, it indicates that the DNA is obtained from a male bird.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference. The full citations of the cited publications are shown preceding the claims.

Example 1

Identifying Sex of Eight Owl Species Using Oligonucleotides W1, W2, W3, ZW1, and ZW2

Eight species of Strigidae, Eurasian-scops Owl (*Otus scops*), Elegant Owl, Brown-wood Owl (*Strix leptogrammica*), Tawny-fish Owl, Collared-scops Owl (*Otus Bakkamoena*), Eurasian-eagle Owl, Mountain-scops Owl (*Otus spilocephalus*), and Short-eared Owl (*Asio flammeus*), were subjected to this study. All of the tested birds were of known sex, as determined by autopsy or behavior.

Genomic DNAs were extracted from the tested birds, in particular, from both muscle samples obtained from carcasses during necropsy or blood samples collected during routine health checkups. Briefly, 0.1 g of muscle or 100 µl of blood was incubated with 20 µl of proteinase K (Amresco, Solon, Ohio) and 500 µl of digestion buffer (10 mM Tris-HCL, 2 mM EDTA, 10 mM NaCl, 1% SDS, 10 mg/ml DTT; Amresco) at 56° C. overnight, followed by phenol/chloroform extraction three times. The aqueous phase was mixed with 100% ethanol at 4° C. for 30 min to precipitate the DNAs contained therein. After centrifugation, the resultant DNA pellet was washed using 70% ethanol, resuspended in 100 µl of 1×TE buffer (Amresco), and passed through a purifying tube (Centricon-100, Amicon, Bedford, England).

The genomic DNA obtained from the procedure described above was used as template for PCR amplification of the CHD1 gene introns flanked by primers 2550F/2718R (Fridolfsson and Ellegren 1999) and by primers 1237L/1272H(Kahn et al. 1998). More specifically, multiplex PCR amplifications, using 5'end-biotinylated 1237L/1272H and 2550F/2718R, were carried out in a reaction mixture (total volume 25 µl) containing 5 µl of each primer (1 µM), 0.5 µl of Taq DNA polymerase (2.5 U/µl), 2.5 µl of 10× PCR buffer (500 mM KCl, 100 mM Tris-HCl pH 8.3, 15 mM MgCl$_2$, 1% Triton X-100, 1600 µg/ml BSA and 2 mM each dNTP, pH 8.2-8.4), and 2 µl of template DNA. The PCR amplification was carried out under the following conditions: 94° C. for 11 min, 30 rounds of 94° C. for 30 s, 50° C. for 30 s, and 72° C. for 60 s, and 72° C. for 5 min. The PCR products thus obtained were separated by agarose gel electrophoresis (3% agarose gel; Gibco, Grand Island, N.Y.) in 0.5×TAE buffer with 0.5 µg/ml of ethidium bromide (Gibco, Grand Island, N.Y.) at 120 V for 1.5 hr.

Figure 1:
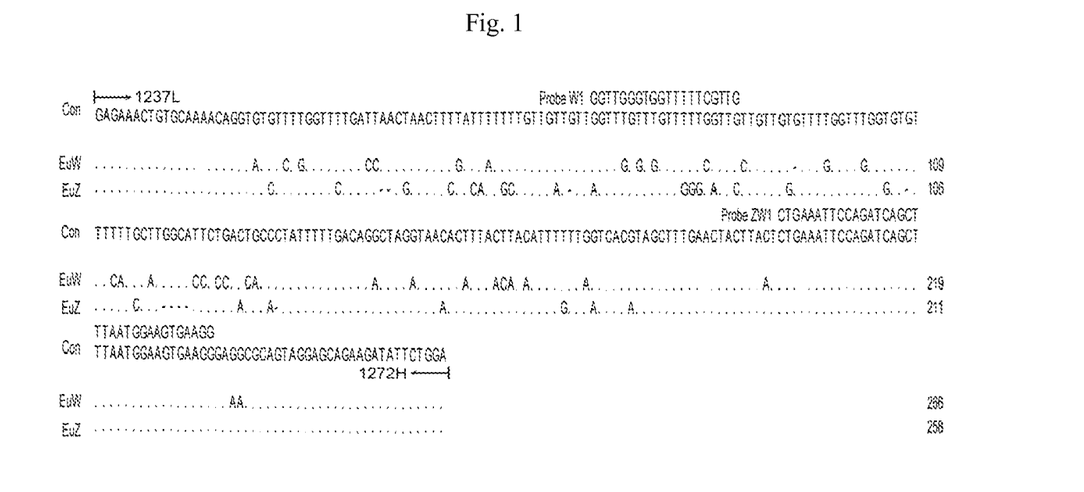
FIG. 1 is a sequence alignment of two DNA fragments amplified from Eurasian-eagle (Eu) owl W (SEQ ID NO: 14) and Z (SEQ ID NO: 15) chromosomes, using primers 1237L/1272H (see Kahn et al., 1998). "Con" refers to the consensus sequence (SEQ ID NO: 13) between the sequences of the two DNA fragments. "." in the sequences of the two DNA fragments refers to nucleotides that are identical to those at the corresponding positions in the consensus sequence; and "-" refers to deletions. The nucleotide sequences of oligonucleotides W1 (SEQ ID NO: 3) and ZW1 (SEQ ID NO: 22) are shown on top of the consensus sequence at the corresponding positions.
Figure 2:
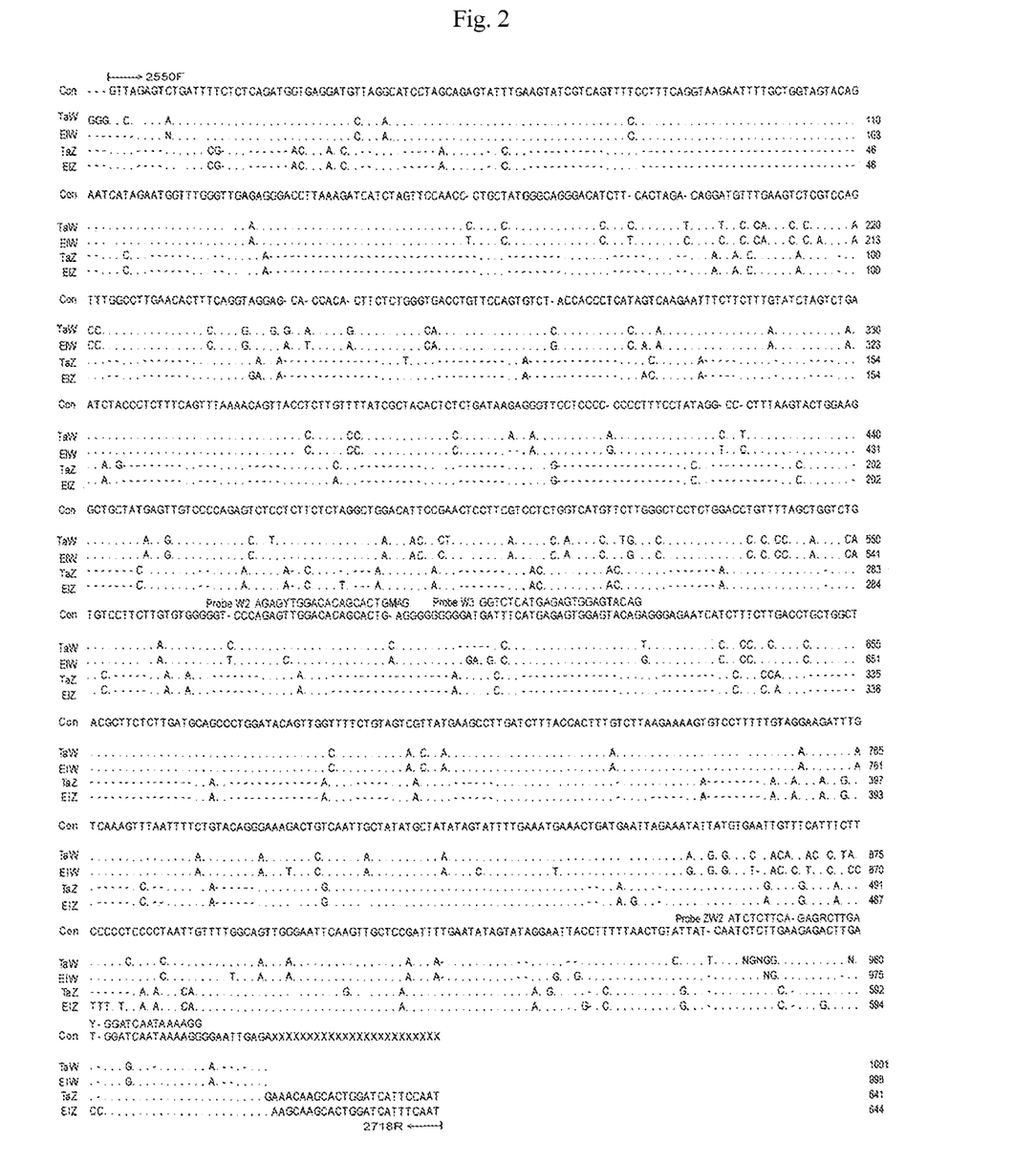
FIG. 2 is a sequence alignment of four DNA fragments amplified from the W and Z chromosomes of Tawny-fish (Ta) owl and Elegant (El) owl (SEQ ID NOS 18-21, respectively in order of appearance), using primers 2550F/2718R (see Fridolfsson et al., 1999). "Con" refers to the consensus sequence (SEQ ID NO: 17) of the nucleotide sequences of the four DNA fragments. "." in the sequences of the four DNA fragments refers to nucleotides that are identical to those at the corresponding positions in the consensus sequence; and "-" refers to deletions. The nucleotide sequences of oligonucleotides W2 (SEQ ID NO: 4), W3 (SEQ ID NO: 5), and ZW2 (SEQ ID NO: 22) are shown on top of the consensus sequence at the corresponding positions.

The PCR products obtained from Eurasian-eagle Owls, Tawny-fish Owls and Elegant Owls, observed using a UV light, were cut, eluted, and subjected to DNA sequencing. Their nucleotide sequences were aligned and analyzed to look for sex-specific probes. See FIGS. 1 and 2. Based on the alignment results, five nucleotide probes, i.e., W1, W2, W3, ZW1, and ZW2 (see FIGS. 1 and 2) were designed for detecting sex-specific fragments of various Strigidae species. More specifically, oligonucleotides W1, W2, and W3 were specific to certain fragments of the W sexual chromosome, which exists only in female birds, while oligonucleotides ZW1 and ZW2 recognize certain fragments of the Z sexual chromosome, which exists in both male and female birds.

A 19-mer poly T tail was added to the 5' end of each of the five oligonucleotides, as well as to a positive control oligo (5'-ATGAAGCATGTCAGGGCTTGGATACCTC G-3') (SEQ ID NO: 12), corresponding to a fragment of the capsid protein VP1 of human enterovirus 71 gene,). Ten µM of each oligonucleotide was then spotted to a specific position on a microarray polymer substrate using an automatic spotting machine (DR. Easy spotter, Miao-Li, Taiwan), and immobilized using a UV Crosslinker (Vilber Lourmat BLX-254, ECC, Marne, France) with 1.2 Joule for 5 min to produce a DNA chip. The chip was then hybridized with the PCR products described above.

The hybridization reaction between each of the PCR products and the DNA chip was carried out with DR. Chip DIY™ Kit (DR. Chip Biotech, Miao-Li, Taiwan) as follows. 15 µl pf each PCR product was denatured at 95° C. for 10 min, and cooled in an ice bath for 2 min, and then contacted in a microarray chamber with the DNA chip in a Hybridization Buffer (200 µl) containing a 5' end-biotinylated oligonucleotide complementary to the sequence of the positive control probe at 50° C. with vibration for 50 min. After being washed twice with a wash Buffer, the DNA chip was then contacted with 0.2 µl of Strep-AP (Streptavidin conjugate alkaline phosphatase) and 200 µl of Blocking Reagent at room temperature for 30 min to block non-specific hybridization. After being washed twice, the chip was subjected to a colorimetric reaction by incubating with 4 µl of NBT/BCIP and 196 µl of Detection Buffer in the chamber in dark at room temperature for 5 min to develop a color pattern on the chip. The color pattern indicates the DNA chip-PCR product hybridization results, and in turn, the sex of the bird from which the PCR product is obtained. More specifically, when the PCR product is hybridizable only to ZW1 or ZW2, it indicates that the PCR product is obtained from a male bird; when the PCR product is hybridizable to both W1, W2, or W3, and ZW1 or ZW2, it indicates that it is obtained from a female bird.

Figure 3:
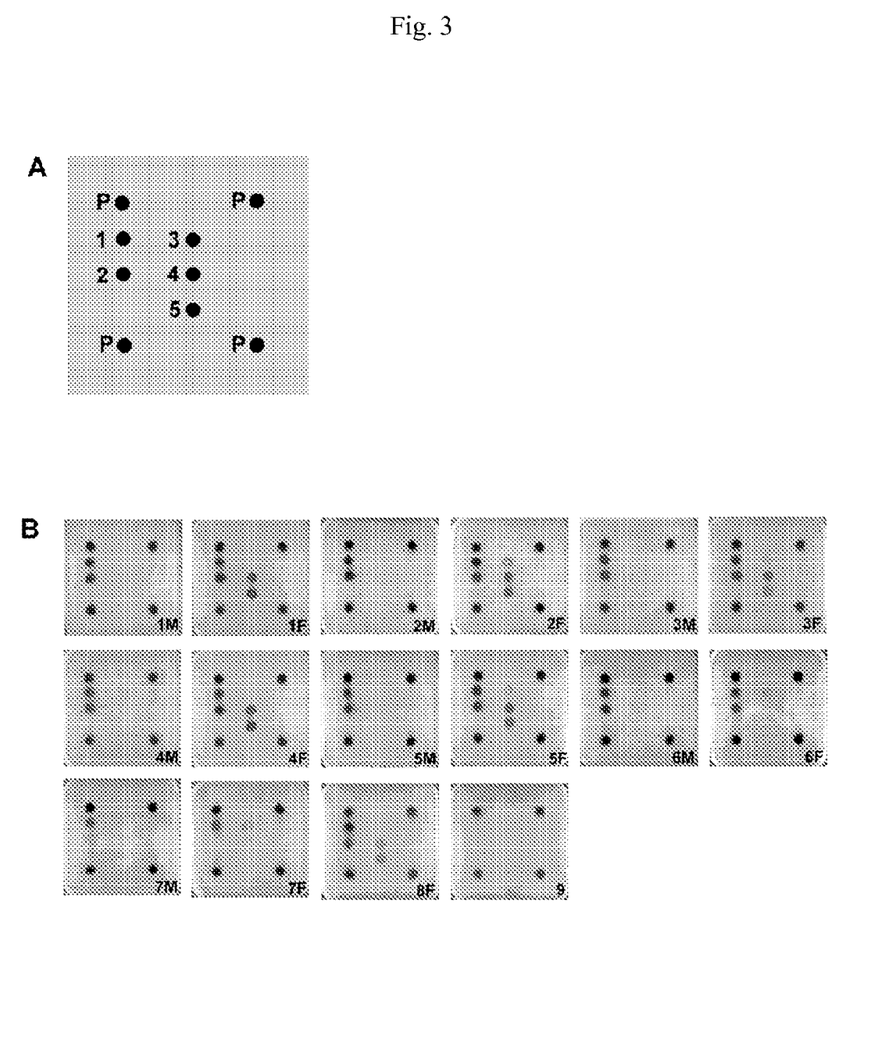
FIG. 3 is a diagram showing sex identification results obtained from hybridizing five bird sex-identification oligonucleotides with DNA fragments amplified from the W and Z sex chromosomes of various owls. A is a map of a microarray chip indicating the positions of the five oligonucleotides contained on the chip. Dot P: Positive control; Dot 1: ZW1; Dot 2: ZW2; Dot 3: W1; Dot 4: W2; and Dot 5: W3. B is a diagram showing hybridization results. M: Male; F: Female. 1: Brown-wood Owl; 2: Tawny-fish Owl; 3: Collared-scops Owl; 4: Eurasian-scops Owl; 5: Elegant owl; 6: Eurasian-eagle Owl; 7: Mountain-scops Owl; 8: Short-eared Owl; and 9: Blank control.

As shown in FIG. 3, the sex of the tested birds (of eight Strigidae species) was successfully identified following the procedures described above. In particular, the PCT products obtained from female birds are hybridizable to both W1, W2, or W3, and ZW1 or ZW2, while the PCR products obtained from male birds are hybridizable only to ZW1 and/or ZW2.

Example 2

Sex Identification of Birds in Various Families Using Nine Sex-Identification Oligonucleotides Both female and male birds of the following species were subjected to this study:
King Penguin (*Aptenodytes patagonicus*; Spheniscidae),
Caribbean Flamingo (*Phoenicopterus rubber*; Phoenicopteridae),
Crested Goshawk (*Accipiter trivirgatus*; Accipitridae),
Swinhoe's Pheasant (*Lophura swinhoii*, Phasianidae),
Helmeted guineafowl (*Numida meleagris*, Numididae),
Sarus Crane (*Grus antigone*, Gruidae),
Nicobar Pigeon (*Caloenas nicobarica*, Columbidae),
Light-vented Bulbul (*Pycnonotus sinensis*, Pycnonotidae),
Formosan Magpie (*Urocissa caerulea*, Corvidae),
Island Canary (*Serinus canaria*, Fringillidae),
Mountain Scops-owl (*Otus spilocephalus*, Strigidae),
Tawny Fish-owl (*Ketupa flavipes*, Strigidae),
Common Flameback (*Dinopium javanense*, Picidae), and
Blue-and-Yellow Macaw (*Ara ararauna*, Psittacidae).

DNA fragments corresponding to the CHD1 gene introns flanked by primers 2550F/2718R and primers 1237L/1272H were obtained from these tested birds via PCR amplification following the same procedures described in Example 1. These DNA fragments were then hybridized with a DNA chip containing the nine sex-identification oligonucleotudes and a control oligonucleotide, all being shown in Table 1 below, under the same hybridization conditions described also in Example 1.

TABLE 1

Sex-Identification Oligonucleotides

| Position on DNA Chip | Names of Oligos | Sequences of Oligos | Gender Specificity | SEQ ID NO: |
|---|---|---|---|---|
| 1 | ZW1 | 5'-CTGRAATTCCAGATCAGCTTYAATGGAARYGAAGG-3' | ♂ and ♀ | 1 |
| 2 | ZW2 | 5'-ATMTCTTYAGAGRCTTGAYGGATCAATAAAAGG-3' | ♂ and ♀ | 2 |
| 3 | W4 | 5'-CTTTTGKGTTGKGTGRTTTT-3' | ♀ only | 6 |
| 4 | W6 | 5'-GGTTGGGTGGTTTTTCGTTG-3' | ♀ only | 3 |

TABLE 1-continued

Sex-Identification Oligonucleotides

| Position on DNA Chip | Names of Oligos | Sequences of Oligos | Gender Specificity | SEQ ID NO: |
|---|---|---|---|---|
| 5 | W7 | 5'-GTTGTTTTGGTCTTTATTTTTGG-3' | ♀ only | 9 |
| 6 | W9 | 5'-ATTTTATTTTATGTACAGGAAAAGACTG-3' | ♀ only | 11 |
| 7 | W8 | 5'-CTGATGAATTAGAAAGATGAARTG-3' | ♀ only | 10 |
| 8 | W5 | 5'-ATTTWTRAAAGTTTMATTTTATGTAYAGRAA-3' | ♀ only | 7 |
| 9 | W3 | 5'-GGTCTCATGAGAGTGGAGTACAG-3' | ♀ only | 5 |
| P | Positive Control | 5'-ATGAAGCATGTCAGGGCTTGGATACCTCG-3' | | 12 |

Figure 4:
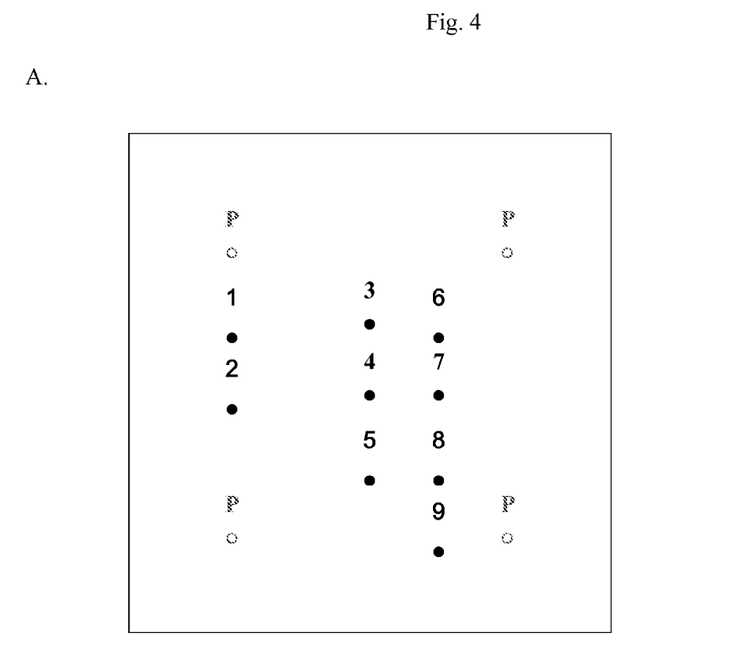
FIG. 4 is a diagram showing sex identification results obtained from hybridizing nine bird sex-identification oligonucleotides with DNA fragments amplified from the W and Z sex chromosomes of birds in various families. A is a map of a microarray chip showing the positions where each of the nine oligonucleotides is spotted. Dot P: positive control oligonucleotide; Dot 1: ZW1; Dot 2: ZW2; Dot 3: W4; Dot 4: W6; Dot 5: W7; Dot 6: W9; Dot 7: W8; Dot 8: W5, and Dot 9: W3. B is a diagram showing hybridization results.

Both the nine sex-identification oligonucleotides and the positive control oligonucleotides were linked to a 19-mer poly (T) tail and immobilized on a DNA chip at positions shown in FIG. 4A. Among the nice sex-identification oligonucleotides, W3-W9 are female bird-specific.

As shown in FIG. 4B, DNA fragments obtained from male birds hybridized with only ZW1 and ZW2, while DNA fragments obtained from female birds hybridized with ZW1 and ZW2, as well as at least one of the female bird-specific oligonucleotides W3-W9. This result indicates that the sex of birds in various families have been successfully determined using these nine sex-identification oligonucleotides.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A kit for determining sex of a bird, comprising:
a first oligonucleotide set including
(i) a first oligonucleotide having the nucleotide sequence of SEQ ID NO: 5 or its complementary sequence;
(ii) a second oligonucleotide having the nucleotide sequence of SEQ ID NO: 6 or its complementary sequence;
(iii) a third oligonucleotide having the nucleotide sequence of SEQ ID NO:7 or its complementary sequence;
(iv) a fourth oligonucleotide having the nucleotide sequence of SEQ ID NO: 8 or its complementary sequence;
(v) a fifth oligonucleotide having the nucleotide sequence of SEQ ID NO: 9 or its complementary sequence;
(vi) a sixth oligonucleotide having the nucleotide sequence of SEQ ID NO: 10 or its complementary sequence; and
(vii) a seventh oligonucleotide having SEQ ID NO: 11 or its complementary sequence; and
  a second oligonucleotide set including (viii) an eighth oligonucleotide having the nucleotide sequence of SEQ ID NO: 1 or its complementary sequences; and (ix) a ninth oligonucleotide having the nucleotide sequence of SEQ ID NO: 2 or its complementary sequence;
wherein each of the oligonucleotides in the first and second sets has up to 60 nucleotides, including an optional linker sequence at the 3' end or 5' end of the oligonucleotide.

2. The kit of claim 1, wherein all of the oligonucleotides are attached to a polymer substrate.

3. The kit of claim 1, wherein the first, second, third, fourth, fifth, sixth, and seventh oligonucleotides respectively include the nucleotide sequences of SEQ ID NOs: 5, 6, 7, 8, 9, 10, and 11, and the eighth and ninth oligonucleotides respectively include the nucleotide sequences of SEQ ID NOs: 1 and 2.

4. The kit of claim 3, wherein all of the oligonucleotides are attached to a polymer substrate.

5. A method for determining sex of a bird, comprising:
providing the kit of claim 1 and a DNA sample obtained from a bird;
hybridizing the DNA sample with the first oligonucleotide set and the second oligonucleotide set; and
determining the sex of the bird, wherein the bird is female if the DNA sample hybridizes to the second oligonucleotide set and to at least one oligonucleotide of the first oligonucleotide set, and the bird is male if the DNA sample hybridizes only to the second oligonucleotide set.

6. The method of claim 5, wherein all of the oligonucleotides are contained in a DNA chip.

7. The method of claim 5, wherein the bird is of a family selected from the group consisting of Accipitridae, Anatidae, Ardeidae, Bucerotidae, Columbidae, Corvidae, Cracidae, Falconidae, Fringillidae, Gruidae, Musophagidae, Numididae, Paradisaeidae, Phalacrocoracidae, Phasianidae, Phoenicopteridae, Picidae, Ploceidae, Procellariidae, Psittacidae, Pycnonotidae, Ramphastidae, Spheniscidae, Strigidae, Threskiornithidae, and Timaliidae.

8. The method of claim 5, wherein the bird is of a family selected from Accipitridae, Columbidae, Corvidae, Fringillidae, Gruidae, Numididae, Phasianidae, Phoenicopteridae, Picidae, Psittacidae, Pycnonotidae, Spheniscidae, and Strigidae.

9. The method of claim 8, wherein the first, second, third, fourth, fifth, sixth, and seventh oligonucletoides respectively include the nucleotide sequences of SEQ ID NOs: 5, 6, 7, 8, 9, 10, and 11; and the eighth and ninth oligonucleotides respectively include the nucleotide sequences of SEQ ID NOs: 1 and 2, all of the oligonucleotides being contained in a DNA chip.

10. The method of claim 7, wherein the bird is a species of Strigidae.

* * * * *